US007189863B2

(12) United States Patent
Ishii et al.

(10) Patent No.: US 7,189,863 B2
(45) Date of Patent: Mar. 13, 2007

(54) PROCESS FOR PRODUCING TRIFLUOROMETHYL-SUBSTITUTED 2-ALKOXYACETOPHENONE DERIVATIVES

(75) Inventors: Akihiro Ishii, Kawagoe (JP); Masatomi Kanai, Kawagoe (JP); Yokusu Kuriyama, Kawagoe (JP); Manabu Yasumoto, Kawagoe (JP); Kenjin Inomiya, Kawagoe (JP); Takashi Ootsuka, Kawagoe (JP); Koji Ueda, Kawagoe (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 11/347,390

(22) Filed: Feb. 6, 2006

(65) Prior Publication Data

US 2006/0128976 A1 Jun. 15, 2006

Related U.S. Application Data

(62) Division of application No. 10/473,399, filed as application No. PCT/JP03/10153 on Aug. 8, 2003.

(30) Foreign Application Priority Data

Aug. 9, 2002 (JP) ............................. 2002-232698
Sep. 6, 2002 (JP) ............................. 2002-261160

(51) Int. Cl.
*C07D 319/06* (2006.01)

(52) U.S. Cl. ...................................................... 549/369

(58) Field of Classification Search ................. 549/369
See application file for complete search history.

(56) References Cited

U.S. PATENT DOCUMENTS 3,717,655 A 2/1973 Godefrol et al.

FOREIGN PATENT DOCUMENTS

| | | |
|---|---|---|
| EP | 0 080 071 A2 | 6/1983 |
| EP | 1 209 150 | 5/2002 |
| JP | 2001-072638 | 3/2001 |
| WO | WO 01/17962 | 8/2000 |

OTHER PUBLICATIONS

Sekimata et al, J. Agric. Food Chem., (2002) vol. 50(12), pp. 3486-3490 (published on the Web May 4, 2002).*

G. Solladie et al, Asymmetric Synthesis of Polyhydroxylated Natural Products I. Efficient Preparation of L-Arabinitol, vol. 28, No. 1, 1987, pp. 61-64, XP0001079307, p. 62, scheme 2.

S. Rozen et al., "A Novel Electrophilic Methoxylation (With a Little Help From F2)", J. Am.Chem. Soc., vol. 114, No. 20, 1992, pp. 7643-7645, XP002260560, scheme II, conversion 15-8.

Database Crossfire, XP-002260564, J. Toullec et al., "Kinetics and Mechanism of the Acid-Catalyzed Bromination of Ring-Substituted Acetophenones in Methanol. Thermodynamics of the Ketone-Acetal-Enol Ether System in Methanol and Water1", J. Org. Chem, vol. 51, No. 21, 1986, pp. 4054-4061, XP002260561.

M. Andersen et al., Electrochemistry of Electron Transfer Probes. Observation of the Transition from Activation to Counterdiffusion Control in the Fragementation of α-Aryloxyacetophenone Radical Anions1a, J. Am. Chem. Soc., vol. 119, No. 28, 1997, pp. 6590-6595, XP002260563, p. 6593, Column 1, p. 6595, Column 2. compounds IVd-e.

Camuzat-Dedenis et al., "Reaction of Phosphonium Ylides and Aromatic Nitriles under Lewis Acid conditions: an Easy Access to Aryl-substituted α-Methoxyacetophenonews" Synthesis (1999) No. 9 pp. 1558-1560.

Lewis et al., "Molecular Photochemistry. XVIII. Type II Photoelimination and 3-Oxetanol Formation from α-Alkoxyacetophenones and Related Compounds" J. Am. Chem. Soc. (1970) 92:311-320.

(Continued)

*Primary Examiner*—Taofiq Solola
(74) *Attorney, Agent, or Firm*—Crowell & Moring LLP

(57) ABSTRACT

A process for producing a brominated acetal (represented by the formula 3) includes (a) brominating a trifluoromethyl-substituted acetophenone by $Br_2$ in the presence of an alkylene diol. It is optional to produce a trifluoromethyl-substituted 2-alkoxyacetophenone derivative (represented by the formula 9) by (b) reacting the brominated acetal with a metal alkoxide, thereby converting the brominated acetal into an ether; and (c) hydrolyzing the ether in the presence of an acid catalyst to remove an acetal group from the ether, thereby producing the 2-alkoxyacetophenone derivative. Alternatively, the 2-alkoxyacetophenone can be produced by (a) reacting a trifluoromethyl-substituted phenacyl halide with an acetalization agent, thereby converting the phenacyl halide into an acetal; (b) reacting the acetal with a metal alkoxide, thereby converting the acetal into an ether; and (c) hydrolyzing the ether in the presence of an acid catalyst to remove the acetal group from the ether

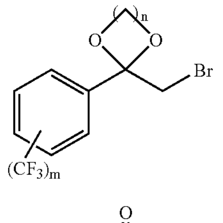

[3]

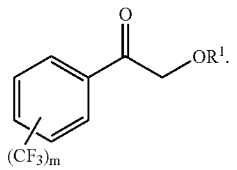

[9]

5 Claims, No Drawings

OTHER PUBLICATIONS

Ferraboschi et al., "Baker's Yeast-Mediated Reduction of α-Hydroxy Ketones and Derivatives: The Steric Course of the Biotransformation" Tetrahedron (1994) vol. 50, No. 35, pp. 10539-10548.

Ashby et al., "The reaction of benzotrihalides and benzal halides with magnesium. Synthetic and mechanistic studies". J. Organometallic Chem., (1990) 390:275-292.

Posner et al., "Methyl and n-alkyl ketones from carboxylic acid chlorides an organocoper reagents" Tetrahedron Letters, No. 53, pp. 4647-4650, (1970).

Greene et al., "Protection for the Carbonyl Group", Protective Groups in Organic Synthesis, Third Edition (1999) pp. 293-368.

Chinese Office Action with English Translation dated Jul. 7, 2006. (Ten (10) Pages).

* cited by examiner

PROCESS FOR PRODUCING TRIFLUOROMETHYL-SUBSTITUTED 2-ALKOXYACETOPHENONE DERIVATIVES

CROSS REFERENCE TO RELATED APPLICATIONS

The present application is a division of application Ser. No. 10/473,399, which is the U.S. national stage of International Application No.: PCT/JP03/10153, filed Aug. 8, 2003, which claims benefit to Japanese priority application nos. 2002-232698, filed Aug. 9, 2002, and 2002-261160, filed Sep. 6, 2002, whose disclosure is hereby incorporated by reference in its entirety into the present application.

BACKGROUND OF THE INVENTION

The present invention relates to a process for producing trifluoromethyl-substituted 2-alkoxyacetophenone derivatives, which are important intermediates for medicines and agricultural chemicals, and to intermediates obtained in the process.

Of trifluoromethyl-substituted 2-alkoxyacetophenone derivatives, only 3'-trifluoromethyl-2-methoxyacetophenone and 4'-trifluoromethyl-2-methoxyacetophenone are known. These compounds can be produced by the following processes. Synthesis (1999), (9), 1558–1560 discloses a process of reacting an ylide (generated from methoxymethyltriphenylphosphonium chloride and phenyl lithium) with 4-trifluoromethylbenzonitrile. Tetrahedron (1979), 35(15), 1807–1815 discloses a process of reacting methoxyacetonitrile with 3-trifluoromethylphenylmagnesium bromide or 4-trifluoromethylphenylmagnesium bromide. J. Am. Chem. Soc. (1970), 92, 311–320 discloses a process of reacting 4'-trifluoromethyl-2-diazoacetophenone with methanol. These processes may not be suitable as industrial production processes for producing trifluoromethyl-substituted 2-alkoxyacetophenone derivatives, due to the use of an expensive reagent excessively and the use of an explosive reagent (see J. Organometallic Chem., 390(1990), 275–292).

Tetrahedron (1994), 50(35), 10539–10548 discloses a reaction of 4-methoxy phenacyl bromide or 4-bromo phenacyl bromide with sodium methoxide.

Japanese Patent Application Publication 2001-72638 discloses a process for producing α-bromoalkylphenones by reacting alkylphenones with bromine in a lower alcohol and then by treating the obtained reaction liquid with an acid. It is disclosed in this publication that specific examples of the lower alcohols are methanol, ethanol and propanol.

SUMMARY OF THE INVENTION

It has been believed that a process of reacting a phenacyl halide with a metal alkoxide to obtain a 2-alkoxyacetophenone derivative is a promising process for industrially producing trifluoromethyl-substituted 2-alkoxyacetophenone derivatives.

Thus, the inventors examined in detail reaction conditions of a process for producing trifluoromethyl-substituted 2-alkoxyacetophenone derivatives by reacting trifluoromethyl-substituted phenacyl halides with metal alkoxides. As a result, it was found that this process is almost incapable of producing the target product and that such reactions of substituted phenacyl halides with metal alkoxides are strongly influenced by changing the type of the substituent (e.g., trifluoromethyl group) on the aryl group of a phenacyl halide. In fact, in the case that the phenacyl halide has such trifluoromethyl substituent, which is a strongly electron attractive group, it was assumed that a nucleophilic attack of the metal alkoxide to the carbonyl group or a deprotonation at the cc-position of the carbonyl group occurs mainly, resulting in a failure to produce the target product.

It is therefore an object of the present invention to provide a process for industrially producing a trifluoromethyl-substituted 2-alkoxyacetophenone derivative.

It is another object of the present invention to provide a process for producing a brominated acetal with high yield, which can be an intermediate for the above trifluoromethyl-substituted 2-alkoxyacetophenone derivative.

According to the present invention, there is provided a first process for producing a brominated acetal represented by the formula 3. The first process comprises the step of (a) brominating a trifluoromethyl-substituted acetophenone, represented by the formula 1, by $Br_2$ in the presence of an acetalization agent that is an alkylene diol represented by the formula 2,

[1]

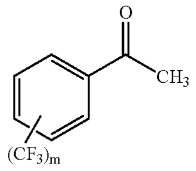

where m represents 1 or 2,

[2]

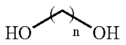

where n represents an integer of from 2 to 4,

[3]

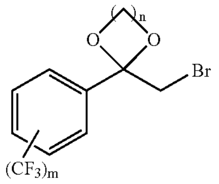

where m and n are respectively defined as in the formulas 1 and 2.

The first process may be a second process for producing a brominated acetal represented by the formula 6. The second process comprises the step of (a) brominating a trifluoromethyl-substituted acetophenone, represented by the formula 4, by $Br_2$ in the presence of an acetalization agent that is an alkylene diol represented by the formula 5.

[4]

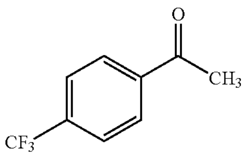

-continued

[5]

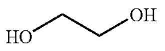

[6]

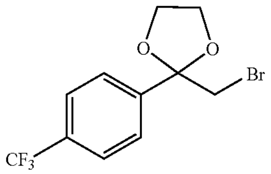

According to the present invention, it is optional to produce a trifluoromethyl-substituted 2-alkoxyacetophenone derivative represented by the formula 9 by a third process. The third process comprises the steps of:

(a) brominating a trifluoromethyl-substituted acetophenone, represented by the formula 1, by $Br_2$ in the presence of an acetalization agent that is an alkylene diol represented by the formula 2, thereby preparing a brominated acetal represented by the formula 3;

(b) reacting the brominated acetal with a metal alkoxide represented by the formula 7, thereby converting the brominated acetal into an ether represented by the formula 8; and (c) hydrolyzing the ether in the presence of an acid catalyst to remove an acetal group from the ether, thereby producing the 2-alkoxyacetophenone derivative.

$R^1OM$ [7]

where $R^1$ represents an alkyl group having a carbon atom number of from 1 to 4, and M represents Li, Na or K,

[8]

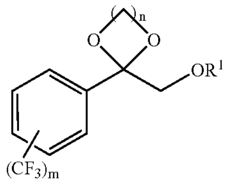

where m, n and $R^1$ are respectively defined as in the formulas 1, 2 and 7,

[9]

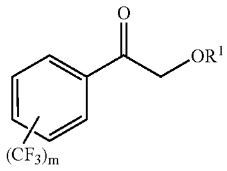

where m and $R^1$ are respectively defined as in the formulas 1 and 7.

As stated above, the third process comprises the step (a), which is identical with that of the first process, and the above additional steps (b) and (c).

According to the present invention, the third process may be a fourth process for producing a trifluoromethyl-substituted 2-alkoxyacetophenone derivative represented by the formula 12. The fourth process comprises the steps of:

(a) brominating a trifluoromethyl-substituted acetophenone, represented by the formula 4, by $Br_2$ in the presence of an acetalization agent that is an alkylene diol represented by the formula 5, thereby preparing a brominated acetal represented by the formula 6;

(b) reacting the brominated acetal with a metal alkoxide represented by the formula 10, thereby converting the brominated acetal into an ether represented by the formula 11; and (c) hydrolyzing the ether in the presence of an acid catalyst to remove an ethylenedioxy group from the ether, thereby producing the 2-alkoxyacetophenone derivative.

$CH_3OM$ [10]

where M represents Na or K,

[11]

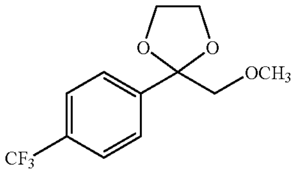

[12]

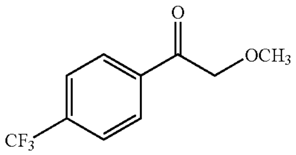

As stated above, the fourth process comprises the step (a), which is identical with the step (a) of the second process, and the above additional steps (b) and (c). Furthermore, the steps (a), (b) and (c) of the fourth process respectively correspond to those of the third process.

According to the present invention, there is provided a fifth process for producing a trifluoromethyl-substituted 2-alkoxyacetophenone derivative represented by the formula 9. The fifth process comprises the steps of:

(a) reacting a trifluoromethyl-substituted phenacyl halide, represented by the formula 13, with an acetalization agent to protect a carbonyl group of the phenacyl halide with an acetal group derived from the acetalization agent, thereby converting the phenacyl halide into an acetal represented by the formula 14;

(b) reacting the acetal with a metal alkoxide represented by the formula 7, thereby converting the acetal into an ether represented by the formula 15; and (c) hydrolyzing the ether in the presence of an acid catalyst to remove the acetal group from the ether, thereby producing the 2-alkoxyacetophenone derivative,

[13]

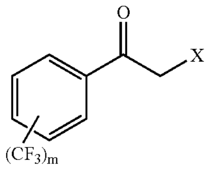

where m represents 1 or 2, and X represents Cl, Br or I,

[14]

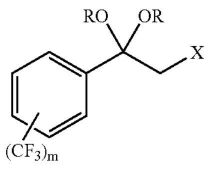

where m and X are defined as in the formula 13, and R represents an alkyl group having a carbon atom number of from 1 to 4, and two of the R optionally form an alkylene group having a carbon atom number of from 2 to 4,

[15]

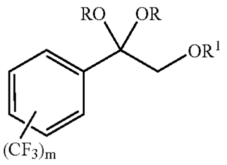

where m, R and $R^1$ are respectively defined as in the formulas 13, 14 and 7.

According to the present invention, the fifth process may be a sixth process for a process for producing a trifluoromethyl-substituted 2-alkoxyacetophenone derivative represented by the formula 12. The sixth process comprises the steps of:

(a) reacting a trifluoromethyl-substituted phenacyl halide, represented by the formula 16, with an acetalization agent to protect a carbonyl group of the phenacyl halide with an ethylenedioxy group derived from the acetalization agent, thereby converting the phenacyl halide into an acetal represented by the formula 17;

(b) reacting the acetal with a methanol solution containing sodium methoxide or potassium methoxide, thereby converting the acetal into an ether represented by the formula 11; and (c) hydrolyzing the ether in the presence of an acid catalyst to remove the ethylenedioxy group from the ether, thereby producing the 2-alkoxyacetophenone derivative.

[16]

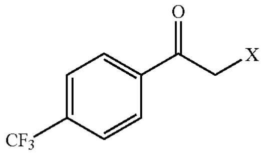

where X represents Cl or Br,

[17]

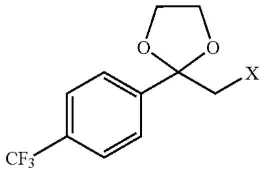

where X is defined as in the formula 16.

The steps (a), (b) and (c) of the sixth process respectively correspond to those of the fifth process.

DESCRIPTION OF THE PREFERRED EMBODIMENTS

As recited in the fifth and sixth processes, the inventors unexpectedly found that, when a trifluoromethyl-substituted phenacyl halide of the formula 13 (particularly a trifluoromethyl-substituted phenacyl bromide) is used as a substrate, the target replacement reaction (i.e., the step (b) of the fifth process) to replace a halogen (X) with an alkoxy group ($—OR^1$) proceeds very well to form an ether of the formula 15 with a high yield by protecting the carbonyl group of the substrate with an acetal group (particularly an alkylenedioxy group), and then the target product (i.e., a trifluoromethyl-substituted 2-alkoxyacetophenone derivative of the formula 9) can be produced with a high yield by hydrolyzing the ether in the presence of an acid catalyst to achieve the deprotection (see the following reaction scheme 1). Each of the protection, the replacement and the deprotection (i.e., the steps (a), (b) and (c) of the fifth and sixth processes) is high in selectivity and does almost not produce impurities difficult for separation. Therefore, each of the fifth and sixth processes is a very effective process for industrially producing a trifluoromethyl-substituted 2-alkoxyacetophenone derivative of the formula 9 or 12.

Reaction Scheme 1

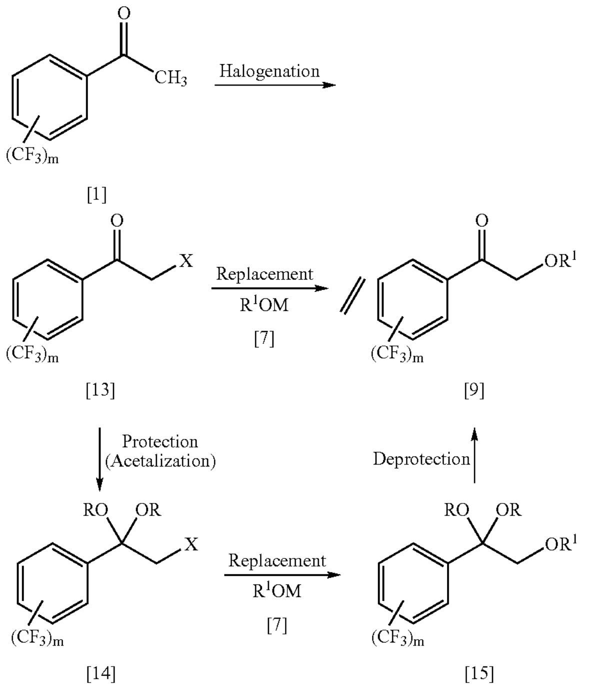

m = 1 or 2 (Each $CF_3$ can take any substitution position.)
X = Cl, Br or I
R = C1–4 alkyl or two of R may form $—(CH_2)_2—$, $—(CH_2)_3—$ or $—(CH_2)_4—$
$R^1$ = C1–4 alkyl
M = Li, Na or K In connection with the first to sixth processes, the present invention provides novel intermediate compounds, that is, acetals represented by the formulas 17 and 18 and ethers represented by the formulas 11 and 15 (the formulas 17, 11 and 15 are recited in the above):

[18]

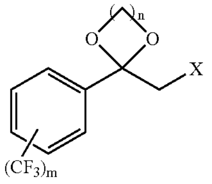

where m represents 1 or 2, X represents Cl, Br or I, and n represents an integer of from 2 to 4.

As recited in the first to fourth processes, the inventors further unexpectedly found that both of the halogenation and the carbonyl group protection proceed simultaneously in one step (i.e., the step (a) of the first to fourth processes) by brominating a trifluoromethyl-substituted acetophenone, represented by the formula 1, by $Br_2$ in the presence of an alkylene diol represented by the formula 2, thereby producing a brominated acetal represented by the formula 3 with high yield (see the following reaction scheme 2).

Reaction Scheme 2

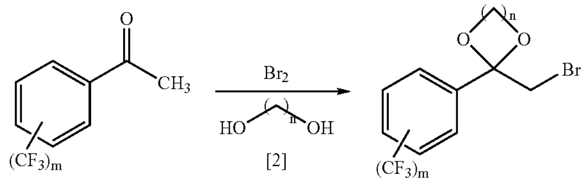

[1] [2] [3]

m = 1 or 2 (Each $CF_3$ can take any substitution position)
n = 2, 3, or 4

In fact, the inventors unexpectedly found in the above bromination that the use of the alkylene diol forms an equilibrium composition (crude reaction product) in which dialkylacetals (e.g., compound C in Table 1) greatly surpass α-bromoacetophenones (e.g., compounds A and D in Table 1) in amount, as compared with the case of using a lower alcohol (e.g., methanol), which is disclosed in Japanese Patent Application Publication 2001-72638. In other words, as shown by the results of Run 2 of Table 1 (the results of Runs 1 and 2 of Table 1 respectively correspond to those of the after-mentioned Comparative Example 1 and Example 1), a crude product obtained by the bromination of the present invention does almost not contain such α-bromoacetophenones, which do not react with a metal alkoxide in the subsequent replacement reaction to produce the target ether. Thus, the crude product is highly suitable for the raw material of the subsequent replacement reaction (i.e., the step (b) of the third or fourth process). The bromination of the present invention produces a brominated acetal of the formula 3 with high yield. Therefore, it is possible to produce the target product, a trifluoromethyl-substituted 2-alkoxyacetophenone of the formula 9, with high yield by subsequently conducting the replacement reaction with a metal alkoxide and the hydrolysis (deprotection).

TABLE 1

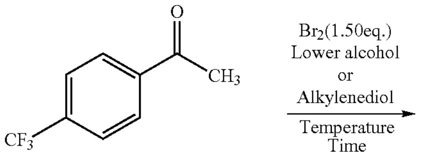

2.82 g
(14.99 mmol)

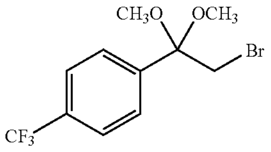

or

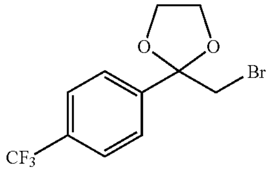

Compound B — Compound C

| Run | Lower alcohol or Alkylenediol | Temperature | Time | Compound A[1,2] | B or C[1,2] | D[1,2] |
|---|---|---|---|---|---|---|
| 1 | $CH_3OH$ | 26–28° C. | 3.5 h | 29.2% | 53.8% | 9.5% |
| | 5.6 ml | | 24 h | 26.0% | 45.3% | 25.3% |
| | (1.4 ml)[3] | | | | | |
| 2 | $HOCH_2CH_2OH$ | 25–28° C. | 3.5 h | 11.7% | 54.2% | 0.3% |
| | 7.5 ml | | 24 h | 3.4% | 88.6% | 0.8% |
| | ($CHCl_3$ 2.2 ml)[3] | | | | | |

[1]Determined by GC.

[2]Compound A

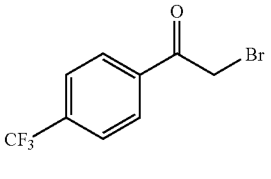

TABLE 1-continued

Compound B

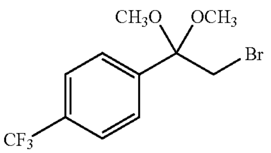

Compound C

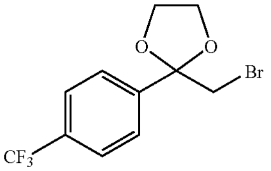

Compound D

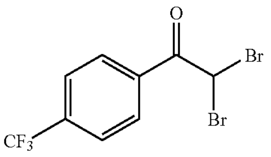

[3]The used amount for preparing dropping $Br_2$ solution.

In general, it is not easy to handle $Br_2$ due to its properties. Thus, it is difficult to precisely control the charged amount of $Br_2$, and it is common to use an excessive amount of $Br_2$ in order to increase yield. In case that $Br_2$ is used in an excessive amount, the use of a lower alcohol (e.g., methanol), which is disclosed in Japanese Patent Application Publication 2001-72638, cannot suppress the generation of α,α-dibromoacetophenones, since the reaction system contains a substantial amount of α-bromoacetophenones. In contrast, in the case of using the alkylene diol according to the present invention, the generation of α,α-dibromoacetophenones does almost not occur, even if $Br_2$ is used in an excessive amount, since dialkylacetals greatly surpass α-bromoacetophenones in amount as mentioned above. Therefore, the bromination of the present invention is a suitable for industrially producing a brominated acetal of the formula 3 or a trifluoromethyl-substituted 2-alkoxyacetophenone derivative of the formula 9.

According to the present invention, it is possible to obtain a brominated acetal (almost not containing α-bromoacetophenones and α,α-dibromoacetophenones) in the step (a) of the first to fourth processes at one time with high yield by brominating the trifluoromethyl-substituted acetophenone by $Br_2$ in the presence of the alkylene diol. Then, the subsequent replacement reaction to replace the bromine with the alkoxy group can proceed very smoothly in the step (b) of the third or fourth process by reacting the brominated acetal with the metal alkoxide, thereby producing a corresponding ether of the formula 8 with high yield. Then, it is possible to produce the target product, the trifluoromethyl-substituted 2-alkoxyacetophenone derivative, with high yield in the step (c) of the third or fourth process by hydrolyzing or deprotecting the ether in the presence of an acid catalyst. Each of these steps (a), (b) and (c) is high in selectively and does almost not produce impurities difficult for separation. Therefore, the first and second processes are very useful for industrially producing the target brominated acetal, and the third and fourth processes are very useful for industrially producing the target trifluoromethyl-substituted 2-alkoxyacetophenone derivative.

The first to fourth processes of the present invention are described in detail as follows (see the following reaction scheme 3).

Reaction Scheme 3

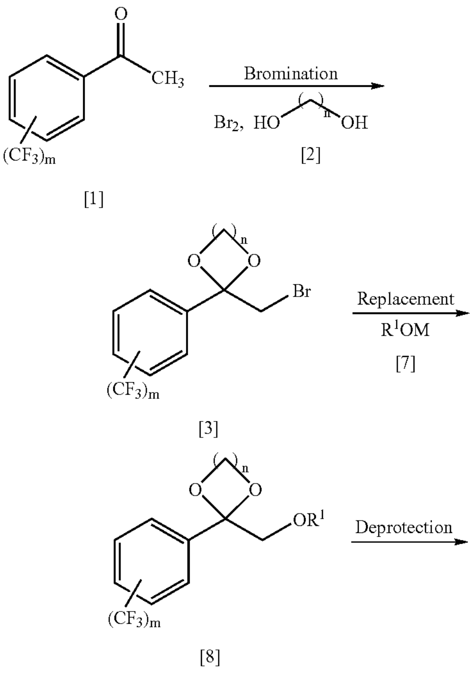

-continued

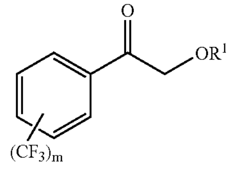

[9]

Firstly, the bromination of the step (a) of the first to fourth processes is described in detail, as follows. The starting raw material, a trifluoromethyl-substituted acetophenone (represented by the formula 1), is selected from 2'-trifluoromethylacetophenone, 3'-trifluoromethylacetophenone, 4'-trifluoromethylacetophenone (represented by the formula 4), 2',3'-bis(trifluoromethyl)acetophenone, 2',4'-bis(trifluoromethyl) acetophenone, 2',5'-bis(trifluoromethyl)acetophenone, 2',6'-bis(trifluoromethyl)acetophenone, 3',4'-bis(trifluoromethyl) acetophenone, and 3',5'-bis(trifluoromethyl)acetophenone. Although some of these compounds are novel compounds, such novel compounds can also be produced, based on the disclosures of Japanese Patent Application Publication 2001-72638 and Tetrahedron Letters No. 53, pp. 4647–4650 (1970), by using substrates having a trifluoromethyl group(s) at a different substitution position(s) on the aryl group.

The alkylene diol (represented by the formula 2) is selected from ethylene glycol (represented by the formula 5), 1,3-propanediol, and 1,4-butanediol. Of these, ethylene glycol and 1,3-propanediol are preferable, and ethylene glycol is more particularly preferable.

The alkylene diol used in the bromination may be in an amount of at least one equivalent, preferably 1–30 equivalents, more preferably 1–20 equivalents, per equivalent of the trifluoromethyl-substituted acetophenone of the formula 1.

$Br_2$ used in the bromination may be in an amount of at least one equivalent, preferably 1–10 equivalents, more preferably 1–5 equivalents, per equivalent of the trifluoromethyl-substituted acetophenone of the formula 1.

It is possible to handle $Br_2$ by dissolving $Br_2$ in a diluting solvent. This diluting solvent may be selected from aliphatic hydrocarbons (e.g., n-pentane, n-hexane, cyclohexane, and n-heptane), halogenated hydrocarbons (e.g., methylene chloride, chloroform, carbon tetrachloride, and 1,2-dichloroethane), ethers (e.g., diethyl ether, tetrahydrofuran, t-butyl methyl ether, and 1,4-dioxane), esters (e.g., ethyl acetate, and n-butyl acetate), nitriles (e.g., acetonitrile and propionitrile), and carboxylic acids (e.g., acetic acid, propionic acid, and butyric acid). Of these, halogenated hydrocarbons and carboxylic acids are preferable, and halogenated hydrocarbons are more preferable.

The way of adding $Br_2$ in the bromination is not particularly limited. For example, a diluted solution of $Br_2$ may be added dropwise to a mixed solution containing the trifluoromethyl-substituted acetophenone and the alkylene diol.

The reaction solvent for conducting the bromination may be the same as the diluting solvent of $Br_2$. Furthermore, the alkylene diol may also be used as a reaction solvent by using it in an excessive amount.

The temperature for conducting the bromination may be from −20° C. to +150° C., preferably −10° C. to +125° C., more preferably from 0° C. to +100° C.

Although the reaction time for conducting the bromination may be from 1 hr to 48 hr, it may be varied depending on the type of the substrate and the reaction conditions. Therefore, it is preferable to terminate the reaction after confirming that the raw material has almost been consumed by checking the progress of the reaction by an analytical means such as gas chromatography, liquid chromatography and NMR.

Post-treatment of the bromination is not particularly limited. An exemplary post-treatment may be conducted as follows. After the reaction, the reaction liquid is added to water or brine, followed by extraction with an organic solvent such as ethyl acetate and toluene. Then, the collected organic layer is dried with a drying agent such as anhydrous sodium sulfate and anhydrous magnesium sulfate, followed by filtration, concentration and vacuum drying, thereby obtaining a crude product. In case that the alkylene diol (particularly ethylene glycol) is used in an excessive amount as a reactant and a reaction solvent of the bromination, the reaction liquid after the reaction separates into two layers. The target product exists only in the lower layer. Therefore, the lower layer can be separated from the upper layer, followed by washing with brine, water or the like, drying with a drying agent (such as anhydrous sodium sulfate and anhydrous magnesium sulfate), filtration and vacuum drying, thereby obtaining a crude product. According to need, the crude product may be subjected to a purification such as activated carbon treatment, distillation, recrystallization, and column chromatography, thereby obtaining a brominated acetal of the formula 3 with high chemical purity. As an alternative to the above post-treatment, it is optional to directly add a metal alkoxide of the formula 7 to the reaction mixture liquid in order to conduct the bromination and the replacement reaction in one pot.

The replacement reaction of the step (b) of the third or fourth process is described in detail, as follows. This reaction can be conducted by reacting a brominated acetal of the formula 3 with a metal alkoxide of the formula 7.

The metal alkoxide of the formula 7 is selected from MeOLi, MeONa and MeOK (represented by the formula 10), EtOLi, EtONa, EtOK, n-PrOLi, n-PrONa, n-PrOK, i-PrOLi, i-PrONa, i-PrOK, n-BuOLi, n-BuONa, n-BuOK, i-BuOLi, i-BuONa, i-BuOK, sec-BuOLi, sec-BuONa, sec-BuOK, tert-BuOLi, tert-BuONa, and tert-BuOK, where Me, Et, Pr and Bu respectively represent methyl group, ethyl group, propyl group, and butyl group. Of these, sodium alkoxides and potassium alkoxides are preferable, and potassium alkoxides are more particularly preferable. The metal alkoxide can easily be prepared from a corresponding alcohol and a metal (Li, Na or K). The metal alkoxide in the form of an alcohol solution may be used in the replacement reaction without conducting its separation from the alcohol solution. It is also possible to use a commercial product of an isolated metal alkoxide (e.g., MeOLi, MeONa, and MeOK) or an alcohol solution of metal alkoxide (e.g., a methanol solution containing 28% MeONa and a methanol solution containing 30% MeOK).

The metal alkoxide used in the replacement reaction may be in an amount of at least 1 equivalent, preferably 1–20 equivalents, more preferably 1–10 equivalents, per equivalent of the brominated acetal of the formula 3.

It is possible to conduct the replacement reaction by adding an additive. This additive may be selected from crown ethers (e.g., 12-crown-4, 15-crown-5, and 18-crown-6), ethylene glycol dialkyl ethers (e.g., 1,2-dimethoxyethane, diethylene glycol dimethyl ether, and triethylene glycol dimethyl ether), and iodides (e.g., sodium iodide, potassium iodide, and tetrabutylammonium iodide). In some cases, it is possible to conduct the replacement reaction more smoothly by using the additive. However, the additive may be omitted provided that the reaction temperature is well controlled. The additive used in the replacement reaction may be in an amount of at least 0.001 equivalents, preferably 0.005–50 equivalents, more preferably 0.01–30 equivalents, per equivalent of the brominated acetal.

The reaction solvent for conducting the replacement reaction may be selected from alcohols (e.g., methanol, ethanol, propanol, isopropanol, butanol, isobutanol, sec-butanol, and tert-butanol), ethers (e.g., diethyl ether, tetrahydrofuran, t-butyl methyl ether, and 1,4-dioxane), and amides (e.g., hexamethylphosphoric triamide, N, N-dimethylformamide, N,N-dimethylacetamide, and N-methylpyrolidone). Of these, alcohols and ethers are preferable, and alcohols are more preferable.

The reaction temperature for conducting the replacement reaction may be from 0° C. to 250° C., preferably 25° C. to 225° C., more preferably 50° C. to 200° C. In case that it is necessary to have a reaction temperature higher than the boiling point of the reaction solution, it is possible to use a pressure-proof reaction vessel.

Although the reaction time for conducting the replacement may be from 6 hr to 48 hr, it may be varied depending on the type of the substrate and the reaction conditions. Therefore, it is preferable to terminate the reaction after confirming that the raw material has almost been consumed by checking the progress of the reaction by an analytical means such as gas chromatography, liquid chromatography and NMR.

Post-treatment of the replacement reaction is not particularly limited. An exemplary post-treatment may be conducted as follows. After the reaction, the reaction liquid is added to water or brine, followed by extraction with an organic solvent (e.g., ethyl acetate and toluene) and washing with water. Then, the collected organic layer is dried with a drying agent such as anhydrous sodium sulfate and anhydrous magnesium sulfate, followed by filtration, concentration and vacuum drying, thereby obtaining a crude product. According to need, the crude product may be subjected to purification such as activated carbon treatment, distillation, recrystallization, and column chromatography, thereby obtaining an ether of the formula 8 with high chemical purity. As an alternative to the above post-treatment, it is optional to directly add an acid catalyst aqueous solution to the reaction mixture liquid in order to conduct the replacement reaction and the deprotection (hydrolysis) in one pot.

The deprotection (hydrolysis) of the step (c) of the third or fourth process is described in detail, as follows. It is possible to conduct the step (c) by reacting the ether, which has been obtained by the step (b), with water in the presence of an acid catalyst.

The acid catalyst may be selected from organic acids (e.g., benzenesulfonic acid, p-toluenesulfonic acid, 10-camphorsulfonic acid, trifluoroacetic acid, and trifluoromethanesulfonic acid) and inorganic acids (e.g., hydrochloric acid, hydrobromic acid, sulfuric acid, and phosphoric acid). Of these, hydrochloric acid and sulfuric acid are preferable, and hydrochloric acid is more preferable.

The acid catalyst used in the deprotection may be in an amount of 100 equivalents or less, preferably 0.01–75 equivalents, more preferably 0.05–50 equivalents, per equivalent of the ether.

The acid catalyst concentration of the aqueous solution may be at least 0.01N, preferably 0.05–20N, more preferably 0.1–12N.

Since the step (c) is a hydrolysis, it is necessary to dissolve the ether in an aqueous solution of an acid catalyst. Therefore, it is possible to more smoothly conduct the reaction by using a solubilizer (dissolution adjuvant) to achieve a uniform dissolution.

The solubilizer may be selected from alcohols (e.g., methanol, ethanol, propanol, and isopropanol) and phase transfer catalysts (e.g., quaternary ammonium salts). Of these, methanol and ethanol are preferable, and methanol is more preferable.

The solubilizer used in the step (c) may be 10 parts by volume or less, preferably 0.001–5.0 parts by volume, more preferably 0.01–3.0 parts by volume, relative to one part by volume of the acid catalyst aqueous solution.

The reaction temperature for conducting the step (c) may be 0–200° C., preferably 0–175° C., more preferably 0–150° C. In case that it is necessary to have a reaction temperature higher than the boiling point of the reaction solution, it is possible to use a pressure-proof reaction vessel.

Although the reaction time for conducting the step (c) may be from 6 hr to 48 hr, it may be varied depending on the type of the substrate and the reaction conditions. Therefore, it is preferable to terminate the reaction after confirming that the raw material has almost been consumed by checking the progress of the reaction by an analytical means such as gas chromatography, liquid chromatography and NMR.

Post-treatment of the step (c) is not particularly limited. An exemplary post-treatment may be conducted as follows. After the reaction, the reaction liquid is added to water or brine, followed by extraction with an organic solvent (e.g., ethyl acetate and toluene) and washing with water. Then, the collected organic layer is dried with a drying agent such as anhydrous sodium sulfate and anhydrous magnesium sulfate, followed by filtration, concentration and vacuum drying, thereby obtaining a crude product. According to need, the crude product may be subjected to purification such as activated carbon treatment, distillation, recrystallization, and column chromatography, thereby obtaining the target product, a trifluoromethyl-substituted 2-alkoxyacetophenone derivative of the formula 9, with high chemical purity.

The fifth and sixth processes of the present invention are described in detail as follows (see the following reaction scheme 4).

Reaction Scheme 4

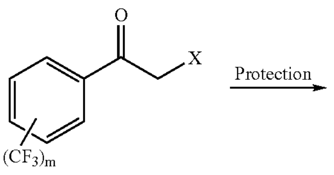

[13]

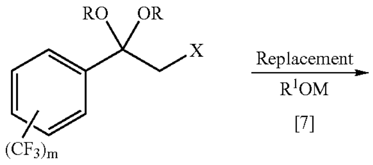

[14]

-continued

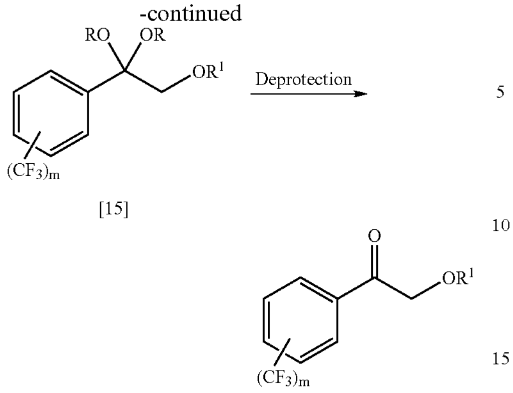

[15]

[9]

The protection (acetalization) of the step (a) of the fifth or sixth process is described in detail as follows. Of compounds corresponding to the trifluoromethyl-substituted phenacyl halide of the formula 13, known compounds are 2-bromo-2'-trifluoromethylacetophenone,
2-chloro-3'-trifluoromethylacetophenone,
2-bromo-3'-trifluoromethylacetophenone,
2-iodo-3'-trifluoromethylacetophenone,
2-chloro-4'-trifluoromethylacetophenone and
2-bromo-4'-trifluoromethylacetophenone (which are represented by the formula 16), 2-iodo-4'-trifluoromethylacetophenone,
2-bromo-2',4'-bis(trifluoromethyl)acetophenone,
2-bromo-3',4'-bis(trifluoromethyl)acetophenone, and
2-bromo-3',5'-bis(trifluoromethyl)acetophenone. In contrast, novel compounds, corresponding to the trifluoromethyl-substituted phenacyl halide of the formula 13, are 2-chloro-2'-trifluoromethylacetophenone,
2-iodo-2'-trifluoromethylacetophenone,
2-chloro-2',3'-bis(trifluoromethyl)acetophenone,
2-bromo-2',3'-bis(trifluoromethyl)acetophenone,
2-iodo-2',3'-bis(trifluoromethyl)acetophenone,
2-chloro-2',4'-bis(trifluoromethyl)acetophenone,
2-iodo-2',4'-bis(trifluoromethyl)acetophenone,
2-chloro-2',5'-bis(trifluoromethyl)acetophenone,
2-bromo-2',5'-bis(trifluoromethyl)acetophenone,
2-iodo-2',5'-bis(trifluoromethyl)acetophenone,
2-chloro-2',6'-bis(trifluoromethyl)acetophenone,
2-bromo-2',6'-bis(trifluoromethyl)acetophenone,
2-iodo-2',6'-bis(trifluoromethyl)acetophenone,
2-chloro-3',4'-bis(trifluoromethyl)acetophenone,
2-iodo-3',4'-bis(trifluoromethyl)acetophenone,
2-chloro-3',5'-bis(trifluoromethyl)acetophenone,
2-iodo-3',5'-bis(trifluoromethyl)acetophenone,
2-chloro-3',6'-bis(trifluoromethyl)acetophenone,
2-bromo-3',6'-bis(trifluoromethyl)acetophenone,
2-iodo-3',6'-bis(trifluoromethyl)acetophenone,
2-chloro-4',6'-bis(trifluoromethyl)acetophenone,
2-bromo-4',6'-bis(trifluoromethyl)acetophenone, and
2-iodo-4',6'-bis(trifluoromethyl)acetophenone.

Of the above compounds corresponding to the trifluoromethyl-substituted phenacyl halide of the formula 13, the 2-chloro derivatives and 2-bromo derivatives can be produced by the same process as those of WO 01/17962 and Japanese Patent Application Publication 2001-72638 using substrates having a trifluoromethyl group(s) at a different substitution position(s) on the aryl group. Furthermore, the 2-iodo derivatives can be produced by conducting halogen exchange of 2-chloro derivatives or 2-bromo derivatives.

The acetalization can be conducted by reacting a trifluoromethyl-substituted phenacyl halide (represented by the formula 13) with an acetalization agent in the presence of an acid catalyst (see Protective Groups in Organic Synthesis, Third Edition, Wiley-Interscience, 1999, p. 293–368).

Examples of an acetal group derived from the acetalization agent include dimethoxy, diethoxy, dipropoxy, diisopropoxy, dibutoxy, diisobutoxy, di-sec-butoxy, di-tert-butoxy, ethylenedioxy, trimethylenedioxy, and tetramethylenedioxy. Of these, dimethoxy and ethylenedioxy are preferable, and ethylenedioxy is more preferable.

Examples of the acetalization agent are methanol, ethanol, propanol, isopropanol, butanol, isobutanol, sec-butanol, tert-butanol, trimethyl orthoformate, triethyl orthoformate, tripropyl orthoformate, triisopropyl orthoformate, tributyl orthoformate, triisobutyl orthoformate, tri-sec-butyl orthoformate, tri-tert-butyl orthoformate, trimethyl orthoacetate, triethyl orthoacetate, tripropyl orthoacetate, triisopropyl orthoacetate, tributyl orthoacetate, triisobutyl orthoacetate, tri-sec-butyl orthoacetate, tri-tert-butyl orthoacetate, ethylene glycol, 1,3-propanediol, and 1,4-butanediol.

The acetalization agent used in the acetalization may be in an amount of one equivalent or more, preferably 1–20 equivalents, more preferably 1–10 equivalents, per equivalent of the trifluoromethyl-substituted phenacyl halide of the formula 13.

As stated above, the acetalization can be conducted in the presence of an acid catalyst. Examples of this acid catalyst include organic acids (e.g., benzenesulfonic acid, p-toluenesulfonic acid, 10-camphorsulfonic acid, trifluoroacetic acid, and trifluoromethanesulfonic acid) and inorganic acids (e.g., hydrochloric acid, hydrobromic acid, sulfuric acid, phosphoric acid, zinc chloride, titanium tetrachloride, and tin tetrachloride). Of these, p-toluenesulfonic acid and sulfuric acid are preferable, and p-toluenesulfonic acid is more preferable.

The acid catalyst used in the acetalization may be in a catalytic amount, preferably 0.001–0.99 equivalents, more preferably 0.005–0.5 equivalents, per equivalent of the trifluoromethyl-substituted phenacyl halide of the formula 13.

An alcohol (e.g., methanol, ethanol, propanol, isopropanol, butanol, isobutanol, sec-butanol, and tert-butanol) as the acetalization agent can be used as a reaction solvent, too. Further preferable examples of the reaction solvent are aromatic hydrocarbons such as toluene, xylene, and mesitylene.

The reaction temperature for conducting the acetalization may be 0–250° C., preferably 25–225° C., more preferably 50–200° C. In case that it is necessary to have a reaction temperature higher than the boiling point of the reaction solution, it is possible to use a pressure-proof reaction vessel.

Although the reaction time for conducting the acetalization may be from 6 hr to 48 hr, it may be varied depending on the type of the substrate and the reaction conditions. Therefore, it is preferable to terminate the reaction after confirming that the raw material has almost been consumed by checking the progress of the reaction by an analytical means such as gas chromatography, liquid chromatography and NMR.

In some cases, water may be produced as a by-product as the acetalization proceeds. In such cases, it is possible to conduct the reaction smoothly by removing such water by using a dehydrator (e.g., zeolite (molecular sieve), phosphorus pentoxide, anhydrous sodium sulfate, and anhydrous magnesium sulfate). Alternatively, such water can be removed from a Dean-Stark tube under reflux condition using an aromatic hydrocarbon reaction solvent (e.g., toluene, xylene, and mesitylene).

Post-treatment of the acetalization is not particularly limited. An exemplary post-treatment may be conducted as follows. After the reaction, the reaction liquid is diluted with an organic solvent (e.g., toluene and ethyl acetate), followed by neutralizing the acid catalyst with a basic aqueous solution (e.g., of sodium hydrogencarbonate or sodium hydroxide) and then washing with water. Then, the collected organic layer is dried with a drying agent such as anhydrous sodium sulfate and anhydrous magnesium sulfate, followed by filtration, concentration and vacuum drying, thereby obtaining a crude product. According to need, the crude product may be subjected to purification such as activated carbon treatment, distillation, recrystallization, and column chromatography, thereby obtaining an acetal of the formula 14 with high chemical purity. As an alternative to the above post-treatment, it is optional to directly add a metal alkoxide of the formula 7 to the reaction mixture liquid in order to conduct the protection and the replacement reaction in one pot.

The steps (b) and (c) (i.e., the replacement reaction and the deprotection) of the fifth or sixth process correspond to the above-described steps (b) and (c) of the third or fourth process. Thus, provided that the brominated acetal of the formula 3 and the ether of the formula 8, which are used in the above description as the raw materials of the steps (b) and (c) of the third or fourth process, are respectively replaced with the acetal of the formula 14 and the ether of the formula 15, all of the above descriptions of the steps (b) and (c) of the third or fourth processes can be applied to those of the steps (b) and (c) of the fifth or sixth process, except the following several modifications. Therefore, the above descriptions of the steps (b) and (c) of the third or fourth process are not repeated hereinafter.

The metal alkoxide used in the replacement reaction (step (b)) of the fifth or sixth process may be in an amount of at least 1 equivalent, preferably 1–20 equivalents, more preferably 1–15 equivalents, per equivalent of the acetal of the formula 14.

The acid catalyst used in the deprotection (step (c)) of the fifth or sixth process may be in an amount of 50 equivalents or less, preferably 0.01–20 equivalents, more preferably 0.05–10 equivalents, per equivalent of the ether of the formula 15.

The acid catalyst concentration of the aqueous solution used in the step (c) of the fifth and sixth processes may be at least 0.01N, preferably 0.05–20N, more preferably 0.1–10N.

The following nonlimitative examples are illustrative of the present invention. In fact, Example 1 is illustrative of the first and second processes, and Comparative Example 1 is not. Example 2 is illustrative of the first to fourth processes. Examples 3–5 are illustrative of the fifth and sixth processes, and Comparative Examples 2–3 are not.

COMPARATIVE EXAMPLE 1

2.82 g (14.99 mmol, 1 eq.) of 4'-trifluoromethylacetophenone were dissolved in 5.6 ml of methanol. While the solution was controlled to have an internal temperature of 26–27° C., a methanol solution obtained by diluting 3.60 g (22.53 mmol, 1.50 eq.) of $Br_2$ with 1.4 ml of methanol was added to the solution, followed by stirring for 24 hr with an internal temperature of 26–28° C. 3.5 hr and 24 hr after the start of the reaction, the progress of the reaction was checked by gas chromatography. The results are shown in Table 2.

TABLE 2

| Time | Compound A[1] | B[1] | D[1] |
|---|---|---|---|
| 3.5 h | 29.2% | 53.8% | 9.5% |
| 24 h | 26.0% | 45.3% | 25.3% |

[1]Compound A

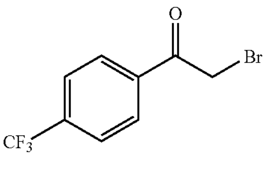

Compound B

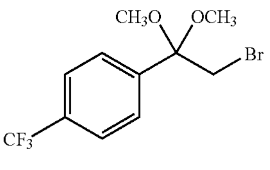

Compound D

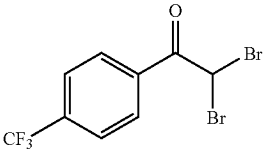

EXAMPLE 1

2.82 g (14.99 mmol, 1 eq.) of 4'-trifluoromethylacetophenone were dissolved in 7.5 ml (8.35 g, 134.53 mmol, 8.97 eq.) of ethylene glycol. While the solution was controlled to have an internal temperature of 25–28° C., a chloroform solution obtained by diluting 3.60 g (22.53 mmol, 1.50 eq.) of $Br_2$ with 2.2 ml of chloroform was added to the solution, followed by stirring for 24 hr with an internal temperature of 25–26° C. 3.5 hr and 24 hr after the start of the reaction, the progress of the reaction was checked by gas chromatography. The results are shown in Table 3.

TABLE 3

| Time | Compound A[1] | C[1] | D[1] |
|---|---|---|---|
| 3.5 h | 11.7% | 54.2% | 0.3% |
| 24 h | 3.4% | 88.6% | 0.8% |

[1]Compound A

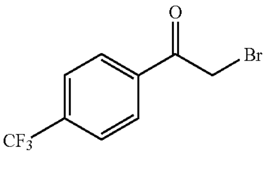

Compound C

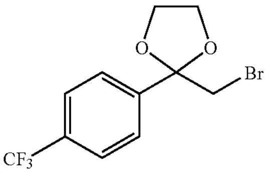

Compound D

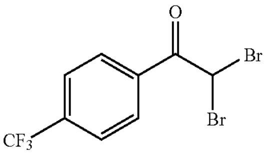

EXAMPLE 2

106 g (0.56 mol, 1 eq.) of 4'-trifluoromethylacetophenone were dissolved in 281 ml (313 g, 5.04 mol, 9.00 eq.) of ethylene glycol. While the solution was controlled to have an internal temperature of 28–32° C., a chloroform solution obtained by diluting 108 g (0.68 mol, 1.21 eq.) of $Br_2$ with 56 ml of chloroform was added to the solution, followed by stirring for 15 hr with an internal temperature of 29–32° C. The resulting reaction separated into an upper and lower layer. Then, the lower layer was washed with 2% brine, followed by drying with anhydrous sodium sulfate, filtration and vacuum drying, thereby obtaining 165 g of a crude product of a brominated acetal represented by the following formula.

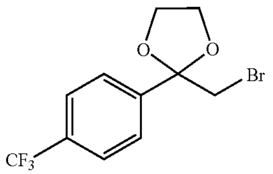

The yield was 94%. The analytical results of the crude product by gas chromatography are shown in Table 4, and its $^1$H-NMR spectrum was as follows.

TABLE 4

| Compound A[1] | C[1] | D[1] | Total Others |
|---|---|---|---|
| 0.6% | 96.9% | 0.9% | 1.6% |

[1]Compound A

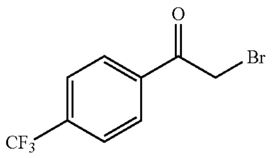

Compound C

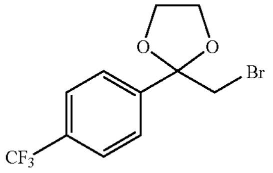

Compound D

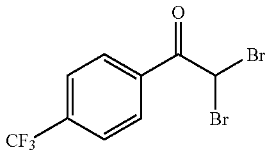

$^1$H-NMR (standard substance: TMS, solvent: $CDCl_3$), δ ppm: 3.64 (s, 2H), 3.83–3.98 (m, 2H), 4.14–4.30 (m, 2H), 7.64 (Ar—H, 4H).

Separately, water was poured into the above-obtained upper layer, followed by extraction with ethyl acetate. The collected organic layer was dried with anhydrous sodium sulfate, followed by filtration, concentration and vacuum drying, thereby obtaining 6 g of a brominated acetal of the above formula. The yield was 3%.

A pressure-proof glass vessel was charged with (a) a part (20.11 g, 64.64 mmol, 1 eq.) of the crude product of the above-obtained lower layer, (b) 75.56 g of a 30% MeOK solution containing 323.23 mmol (5.00 eq.) of MeOK dissolved in methanol, and (c) 11.65 g (129.27 mmol, 2.00 eq.) of 1,2-dimethoxyethane, followed by stirring for 15 hr at 140° C. After the reaction, the reaction liquid was poured into a saturated brine, followed by extraction with ethyl acetate. The collected organic layer was dried with anhydrous sodium sulfate, followed by filtration, concentration and vacuum drying, thereby obtaining 18.12 g of a crude product of an ether represented by the following formula.

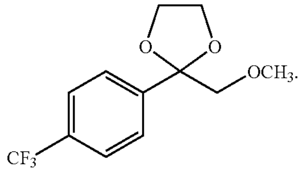

Conversion and selectivity of the reaction were found by gas chromatography to be 99% and 97%, respectively. $^1$H-NMR spectrum of the crude product was as follows.

$^1$H-NMR (standard substance: TMS, solvent: $CDCl_3$), δ ppm: 3.40 (s, 3H), 3.60 (s, 2H), 3.79–3.93 (m, 2H), 4.06–4.20 (m, 2H), 7.55–7.72 (Ar—H, 4H).

The total amount (18.12 g, 64.64 mmol, 1 eq.) of the above crude product of the ether and 242.40 ml of 8N HCl (containing 1939.20 mmol (30.00 eq.) of HCl) were added to 242.4 ml of methanol, followed by stirring for 36 hr at room temperature. After the reaction, the reaction liquid was poured into a saturated brine, followed by extraction with ethyl acetate. The collected organic layer was dried with anhydrous sodium sulfate, followed by filtration, concentration and vacuum drying, thereby obtaining 15.63 g of a crude product of a trifluoromethyl-substituted 2-alkoxyacetophenone derivative represented by the following formula.

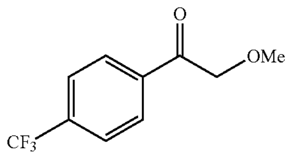

Conversion of the reaction was found by gas chromatography to be 99%. The crude product was found by a quantitative analysis with $^{19}$F-NMR internal standard method to contain 12.07 g of the target product. The total yield from the bromination to the deprotection was 83%. The total amount (15.63 g) of the crude product was recrystallized from n-hexane (1.5 times that of the crude product in volume), thereby obtaining 9.31 g of a purified product (gas chromatographic purity: higher than 99.7%). $^1$H-NMR spectrum of the product was as follows:

$^1$H-NMR (standard substance: TMS, solvent: $CDCl_3$), δ ppm: 3.52 (s, 3H), 4.70 (s, 2H), 7.75 (d, 8.6 Hz, 2H), 8.06 (d, 8.6 Hz, 2H).

COMPARATIVE EXAMPLE 2

A pressure-proof glass vessel was charged with 1.00 g (3.74 mmol, 1 eq.) of 2-bromo-4'-trifluoromethylacetophenone and 4.38 g of 30% MeOK solution containing 18.74 mmol (5.01 eq.) of MeOK dissolved in methanol, followed by stirring for 24 hr at room temperature. After the reaction, the reaction liquid was poured into a saturated brine, followed by extraction with ethyl acetate. The collected organic layer was dried with anhydrous sodium sulfate, followed by filtration, concentration and vacuum drying, thereby obtaining 0.94 g of a crude product of a trifluoromethyl-substituted 2-alkoxyacetophenone derivative represented by the following formula.

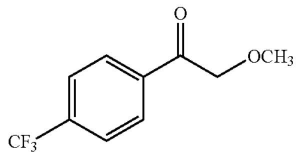

As a result of an analysis of the crude product with gas chromatography and $^{1}$H-NMR and $^{19}$F-NMR, it was found that the raw material had almost been consumed (conversion>95%). However, the yield was found by a $^{19}$F-NMR internal standard method to be less than 5%.

COMPARATIVE EXAMPLE 3

A pressure-proof glass vessel was charge with 1.00 g (4.49 mmol, 1 eq.) of 2-chloro-4'-trifluoromethylacetophenone and 5.25 g of 30% MeOK solution containing 22.46 mmol (5.00 eq.) of MeOK dissolved in methanol, followed by stirring for 24 hr at room temperature. After the reaction, the reaction liquid was poured into a saturated brine, followed by extraction with ethyl acetate. The collected organic layer was dried with anhydrous sodium sulfate, followed by filtration, concentration and vacuum drying, thereby obtaining 0.89 g of a crude product of a trifluoromethyl-substituted 2-alkoxyacetophenone derivative represented by the following formula.

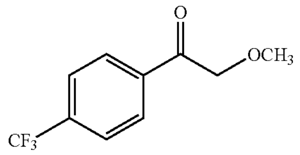

As a result of an analysis of the crude product with gas chromatography and $^{1}$H-NMR and $^{19}$F-NMR, it was found that the raw material had almost been consumed (conversion>95%). However, the yield was found by a $^{19}$F-NMR internal standard method to be less than 5%.

EXAMPLE 3

To 200 ml of toluene, 7.11 g (26.63 mmol, 1 eq.) of 2-bromo-4'-trifluoromethylacetophenone, 4.96 g (79.91 mmol, 3.00 eq.) of ethylene glycol, and 0.51 g (2.68 mmol, 0.10 eq.) of p-toluenesulfonic acid monohydrate were added. The mixture was stirred for 14 hr under heated reflux, and water as a by-product was removed from a Dean-Stark tube. After the reaction, the reaction liquid was washed with a saturated sodium hydrogencarbonate aqueous solution and then a saturated brine. The collected organic layer was dried with anhydrous sodium sulfate, followed by filtration, concentration and vacuum drying, thereby obtaining 8.33 g of a crude product of an acetal represented by the following formula.

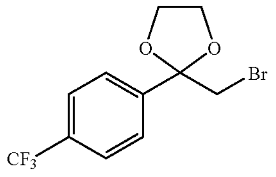

The yield was quantitative. $^{1}$H-NMR spectrum of the product was as follows:

$^{1}$H-NMR (TMS, $CDCl_3$): 3.64 (s, 2H), 3.83–3.98 (m, 2H), 4.14–4.30 (m, 2H), 7.64 (Ar—H, 4H).

Then, a pressure-proof glass vessel was charged with a part (3.31 g, 10.58 mmol, 1 eq.) of the above crude product and 23.56 g of 30% MeOK solution containing 100.78 mmol (9.53 eq.) of MeOK dissolved in methanol, followed by stirring at 140° C. for 24 hr. After the reaction, the reaction liquid was poured into a saturated brine, followed by extraction with ethyl acetate. The collected organic layer was dried with anhydrous sodium sulfate, followed by filtration, concentration and vacuum drying, thereby obtaining 2.87 g of a crude product of an ether represented by the following formula.

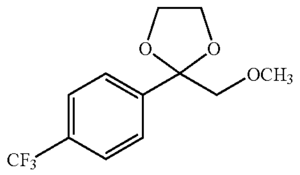

Conversion and selectivity of the reaction were found by gas chromatography to be 97% and 93%, respectively. $^{1}$H-NMR spectrum of the product was as follows:

$^{1}$H-NMR (TMS, $CDCl_3$): 3.40 (s, 3H), 3.60 (s, 2H), 3.79–3.93 (m, 2H), 4.06–4.20 (m, 2H), 7.55–7.72 (Ar—H, 4H).

Then, the total amount (2.87 g, 10.58 mmol, 1 eq.) of the above crude product of the ether and 5.32 ml of 6N HCl containing 31.92 mmol (3.02 eq.) of HCl were added to 5.3 ml of methanol, followed by stirring at room temperature for 36 hr. After the reaction, the reaction liquid was poured into a saturated brine, followed by extraction with ethyl acetate. The collected organic layer was dried with anhydrous sodium sulfate, followed by filtration, concentration and vacuum drying, thereby obtaining 2.39 g of a crude product of a trifluoromethyl-substituted 2-alkoxyacetophenone derivative represented by the following formula.

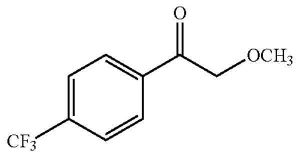

Conversion of the reaction was found by gas chromatography to be 99%. The above crude product was found by a quantitative analysis with $^{19}$F-NMR internal standard method to contain 1.87 g of the target product. The total yield from the protection to the deprotection was 81%. The total amount (1.87 g) of the crude product was recrystallized from n-pentane (1.5 times that of the crude product in volume), thereby obtaining 1.02 g of a purified product (gas chromatographic purity: higher than 99.5%). $^1$H-NMR spectrum of the product was the same as that of the final product of Example 2.

EXAMPLE 4

A pressure-proof glass vessel was charged with a part (3.66 g, 11.70 mmol, 1 eq.) of the crude product of the acetal obtained in Example 3 and 22.69 g of 28% MeONa solution containing 117.61 mmol (10.05 eq.) of MeONa dissolved in methanol, followed by stirring at 145° C. for 36 hr. After the reaction, the reaction liquid was poured into a saturated brine, followed by extraction with ethyl acetate. The collected organic layer was dried with anhydrous sodium sulfate, followed by filtration, concentration and vacuum drying, thereby obtaining 3.45 g of a crude product of an ether represented by the following formula.

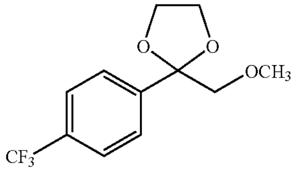

Conversion and selectivity of the reaction were found by gas chromatography to be 75% and 86%, respectively. $^1$H-NMR spectrum of the product was the same as the crude product of the ether obtained in Example 3.

Then, the total amount (3.45 g, 11.70 mmol, 1 eq.) of the above crude product of the ether and 5.88 ml of 6N HCl containing 35.28 mmol (3.02 eq.) of HCl were added to 5.9 ml of methanol, followed by stirring at room temperature for 36 hr. After the reaction, the reaction liquid was poured into a saturated brine, followed by extraction with ethyl acetate. The collected organic layer was dried with anhydrous sodium sulfate, followed by filtration, concentration and vacuum drying, thereby obtaining 5.21 g of a crude product of a trifluoromethyl-substituted 2-alkoxyacetophenone derivative represented by the following formula.

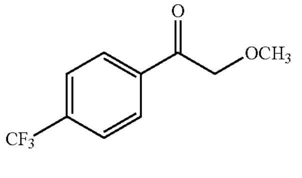

Conversion of the reaction was found by gas chromatography to be 98%. The above crude product was found by a quantitative analysis with $^{19}$F-NMR internal standard method to contain 1.32 g of the target product. The total yield from the protection to the deprotection was 52%. $^1$H-NMR spectrum of the product was the same as that of the final product of Example 2.

EXAMPLE 5

To 200 ml of toluene, 5.98 g (26.87 mmol, 1 eq.) of 2-chloro-4'-trifluoromethylacetophenone, 5.00 g (80.55 mmol, 3.00 eq.) of ethylene glycol, and 0.51 g (2.68 mmol, 0.10 eq.) of p-toluenesulfonic acid monohydrate were added. The mixture was stirred for 18 hr under heated reflux, and water as a by-product was removed from a Dean-Stark tube. After the reaction, the reaction liquid was washed with a saturated sodium hydrogencarbonate aqueous solution and then a saturated brine. The collected organic layer was dried with anhydrous sodium sulfate, followed by filtration, concentration and vacuum drying, thereby obtaining 7.43 g of a crude product of an acetal represented by the following formula.

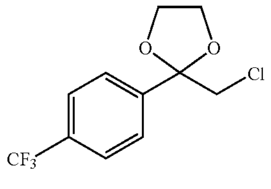

The yield was quantitative. $^1$H-NMR spectrum of the product was as follows: $^1$H-NMR (standard substance: TMS, solvent: $CDCl_3$): 3.74 (s, 2H), 3.83–3.99 (m, 2H), 4.09–4.30 (m, 2H), 7.64 (Ar—H, 4H).

Then, a pressure-proof glass vessel was charged with (a) a part (5.44 g, 19.67 mmol, 1 eq.) of the above crude product and (b) 47.69 g of 30% MeOK solution containing 204.01 mmol (10.37 eq.) of MeOK dissolved in methanol, followed by stirring at 140° C. for 34 hr. After the reaction, the reaction liquid was poured into a saturated brine, followed by extraction with ethyl acetate. The collected organic layer was dried with anhydrous sodium sulfate, followed by filtration, concentration and vacuum drying, thereby obtaining 2.87 g of a crude product of an ether represented by the following formula.

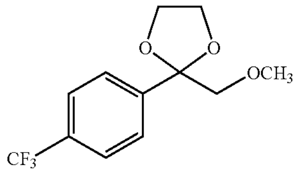

Conversion and selectivity of the reaction were found by gas chromatography to be 52% and 88%, respectively. $^1$H-NMR spectrum of the product was the same as that of the crude product of the ether obtained in Example 3.

Then, the total amount (5.21 g, 19.67 mmol, 1 eq.) of the above crude product of the ether and 10.20 ml of 6N HCl containing 61.20 mmol (3.11 eq.) of HCl were added to 10.2 ml of methanol, followed by stirring at room temperature for 38 hr. After the reaction, the reaction liquid was poured into a saturated brine, followed by extraction with ethyl acetate. The collected organic layer was dried with anhydrous sodium sulfate, followed by filtration, concentration and vacuum drying, thereby obtaining 4.18 g of a crude product of a trifluoromethyl-substituted 2-alkoxyacetophenone derivative represented by the following formula.

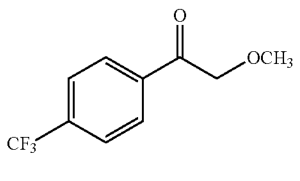

Conversion of the reaction was found by gas chromatography to be 99%. The above crude product was found by a quantitative analysis with $^{19}F$-NMR internal standard method to contain 1.55 g of the target product. The total yield from the protection to the deprotection was 36%. $^{1}H$-NMR spectrum of the product was the same as that of the final product of Example 2.

What is claimed is:

1. A process for producing a brominated acetal represented by the formula 3, comprising the step of (a) brominating a trifluoromethyl-substituted acetophenone, represented by the formula 1, by $Br_2$ in the presence of an acetalization agent that is an alkylene diol represented by the formula 2,

[1]

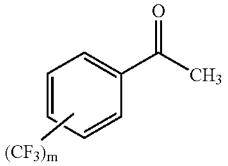

where m represents 1 or 2,

[2]

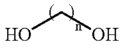

where n represents an integer of from 2 to 4,

[3]

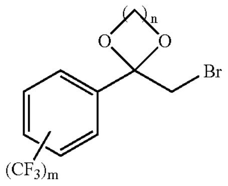

where m and n are respectively defined as in the formulas 1 and 2.

2. A process for producing a brominated acetal represented by the formula 6, comprising the step of (a) brominating a trifluoromethyl-substituted acetophenone, represented by the formula 4, by $Br_2$ in the presence of an acetalization agent that is an alkylene diol represented by the formula 5.

[4]

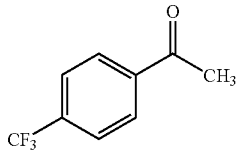

[5]

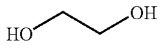

[6]

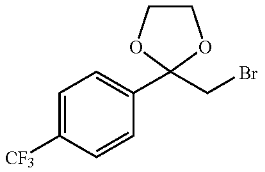

3. A process according to claim 1, wherein the acetalization agent is ethylene glycol.

4. An ether represented by the formula 15,

[15]

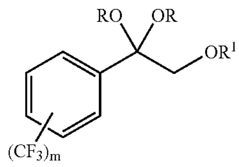

where m represents 1 or 2, R represents an alkyl group having a carbon atom number of from 1 to 4, and two of the R optionally form an alkylene group having a carbon atom number of from 2 to 4, and $R^1$ represents an alkyl group having a carbon atom number of from 1 to 4.

5. An ether represented by the formula 11.

[11]

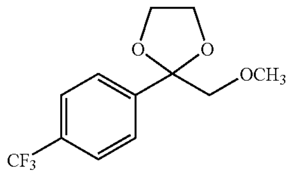

* * * * *